US00PP37396P2

(12) United States Plant Patent
Boxriker

(10) Patent No.: US PP37,396 P2
(45) Date of Patent: Apr. 28, 2026

(54) ***DAHLIA* PLANT NAMED 'KLEDH24733'**

(50) Latin Name: ***Dahlia* sp.**
Varietal Denomination: KLEDH24733

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/320,816

(22) Filed: Sep. 5, 2025

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

(56) References Cited

U.S. PATENT DOCUMENTS

PP23,114 P2 * 10/2012 Nielsen ..... A01H 6/14
Plt./321

* cited by examiner

*Primary Examiner* — Susan Mccormick Ewoldt
(74) *Attorney, Agent, or Firm* — Weatherly IP Solutions, LLC; Karen P. Bechtold; James M. Weatherly

(57) ABSTRACT

A new *Dahlia* plant named 'KLEDH24733' particularly distinguished by large white flowers and composite head inflorescence, double, held above the foliage, as described herein.

1 Drawing Sheet

Genus and species: *Dahlia* sp.
Variety denomination: 'KLEDH24733'.

BACKGROUND

The present invention comprises a new and distinct variety of *Dahlia*, botanically known as *Dahlia* sp., and hereinafter referred to by the variety name 'KLEDH24733'. 'KLEDH24733' originated from an open pollination with the female *Dahlia* 'DH-2015-2014' (unpatented) and an unknown male *Dahlia* plant in Summer 2020 in Latina, Italy. In March 2021, in Latina, Italy, a seedling was selected and named 'KLEDH24733'. 'KLEDH24733' was first vegetatively propagated by vegetative cuttings in April 2021 in Latina, Italy. 'KLEDH24733' was found to reproduce true to type in successive generations of asexual propagation.

SUMMARY

The following are the most outstanding and distinguishing characteristics of 'KLEDH24733' when grown under normal horticultural practices in Latina, Italy.

1. Large white flowers
2. A composite head inflorescence, double, held above the foliage

DESCRIPTION OF THE PHOTOGRAPH

This new *Dahlia* plant is illustrated by the accompanying photograph of the plant approximately fourteen weeks old and grown in a greenhouse in Stuttgart, Germany. The photograph shows the whole plant, including the inflorescences and foliage and buds and was taken in May 2024 in Stuttgart, Germany. The colors shown are as true as can be reasonably obtained by conventional photographic procedures.

DESCRIPTION OF 'KLEDH24733'

The following detailed descriptions set forth the distinctive characteristics of 'KLEDH24733'. The data which define these characteristics were collected from asexual reproductions from 16-week-old plants grown in a greenhouse in Latina, Italy. Color references are to The R.H.S. Colour Chart of The Royal Horticultural Society of London (R.H.S.), 5$^{th}$ edition (2007).

Classification:
*Family*.—Asteraceae.
*Botanical*.—*Dahlia* sp.
*Designation*.—'KLEDH24733'.

Parentage:
*Female parent*.—'DH-2015-2014' (unpatented).
*Male parent*.—Unknown male parent.

Propagation:
*Type*.—Vegetative terminal cuttings.
*Time to produce a rooted young plant*.—3 to 4 weeks.
*Time to produce a flowering plant*.—About 10 weeks.
*Root description*.—RHS N155C in color, fine.
*Rooting habit*.—Freely branching and moderately dense.

Plant description:
*Plant and growth habit*.—Compact and semi-upright.
*Plant height*.—To the top of foliar plane: About 18.0 cm. Including inflorescence: About 32.0 cm.
*Plant diameter*.—About 25.0 cm.

Lateral branches:
*Length*.—Up to the last pair of leaves: About 13.5 cm. Including inflorescence: About 18.0 cm.

*Diameter.*—0.3 cm.
*Internode length.*—2.2 cm to 5.5 cm.
*Strength.*—Medium strong.
*Texture.*—Smooth.
*Color.*—Close to RHS 144A.

Foliage description:
*Arrangement.*—Opposite, pinnate.
*Length.*—About 11.0 cm.
*Width.*—Up to 9.0 cm.
*Shape.*—Pinnate.
*Apex.*—Acute.
*Base.*—Truncate.
*Margin.*—Serrate.
*Venation pattern.*—Pinnate.
*Venation color.*—RHS 146A.
*Texture.*—Upper and lower surface: Slightly hairy on the edges, slightly rugose and glossy.
*Color.*—Immature: Upper surface: RHS N137B. Lower surface: Close to RHS N138B. Mature: Upper surface: RHS N137C. Lower surface: Close to RHS 148C.

Petioles:
*Length.*—About 2.5 cm.
*Diameter.*—0.25 cm in the mid-section, 0.5 cm at the node.
*Texture.*—Upper surface: Smooth. Lower surface: Smooth.
*Color.*—Upper surface: RHS 146C. Lower surface: RHS 146C/RHS 146D.

Inflorescence description:
*Appearance and arrangement.*—Composite head inflorescence, double, held above the foliage.
*Fragrance.*—Not detected.
*Time to flower.*—About 10 weeks after potting.
*Post-production longevity.*—Plants flower continuously from spring through autumn.

Inflorescence bud:
*Height.*—1.5 cm.
*Diameter.*—1.5 cm.
*Shape.*—Globular.
*Color.*—RHS 137A at the base and RHS 144C toward the tips.

Inflorescence size:
*Diameter.*—7.0 cm.
*Depth* (*height*).—2.8 cm.
*Disc diameter.*—Not visible.
*Receptacle height.*—0.4 cm.
*Receptacle diameter.*—2.0 cm.
*Receptacle color.*—RHS 144A.

Ray florets:
*Quantity per inflorescence.*—Approximately 85 in about 7 whorls.
*Length.*—Up to 3.3 cm.
*Width.*—Up to 1.8 cm.
*Shape.*—Ligulate, obovate.
*Apex.*—Slightly dentate.
*Base.*—Fused in a tube.
*Margin.*—Entire.
*Aspect.*—Keeled.
*Texture.*—Upper surface: Smooth. Lower surface: Smooth.
*Color.*—Immature: Upper surface: RHS 155C. Lower surface: RHS 155C. Mature: Upper surface: RHS NN155C. Lower surface: RHS NN155C.

Disc florets:
*Quantity per inflorescence.*—About 16.
*Length.*—About 1.0 cm.
*Diameter.*—About 0.2 cm.
*Shape.*—Tubular.
*Texture.*—Inner surface: Smooth. Outer surface: Smooth.
*Color.*—Immature: Inner surface: RHS 1D. Outer surface: RHS 1D. Mature: Inner surface: RHS 1A. Outer surface: RHS 1B.

Phyllaries:
*Quantity per inflorescence.*—5 at the external whorl, about 13 in the internal whorl.
*Length.*—1.8 cm.
*Width.*—0.6 cm.
*Shape.*—Lanceolate.
*Apex.*—Acute.
*Base.*—External: Attenuate. Internal: Fused.
*Margin.*—Entire.
*Texture.*—Upper surface: Smooth and slightly glossy. Lower surface: Smooth and slightly glossy.
*Color.*—Upper surface: External whorl: RHS 137A. Internal whorl: RHS 144A at the base to N144D at the tips. Lower surface: External whorl: RHS N137B. Internal whorl: RHS 144A at the base to RHS N144D at the tips.

Peduncles:
*Length, terminal peduncle.*—13.5 cm.
*Length, axillary peduncle.*—Up to 8.0 cm.
*Diameter.*—0.2 cm.
*Aspect.*—Upright.
*Strength.*—Strong.
*Texture.*—Smooth.
*Color.*—RHS 144D.

Reproductive organs:
*Androecium.*—Presence: Only on disc florets. Quantity per floret: 5 stamens with fused anthers. Filament length: 0.3 cm. Filament color: RHS 2C. Anther shape: Oblong. Anther length: 0.4 cm. Anther color: RHS 15A. Pollen amount: Average. Pollen color: RHS 15A.
*Gynoecium.*—Quantity per floret: 1. Pistil length: About 0.7 cm. Style length: 0.3 cm. Style color: RHS 2B. Stigma shape: Bipartite. Stigma color: RHS 13A. Ovary color: RHS 145D.

Fruit and seed set: Not observed during growing season.

Disease and pest/insect resistance: No disease resistance observed.

COMPARISON OF 'KLEDH24733' WITH PARENTAL LINE AND KNOWN VARIETY

'KLEDH24733' is distinguished from the parent as described in Table 1.

TABLE 1

| Comparison with Parental Line | | |
|---|---|---|
| Trait | Variety 'KLEDH24733' | Female parent 'DH-2015-2014' (unpatented) |
| Habit and flower size | More compact and bigger flowers than 'DH-2015-2014' | More vigorous and smaller flowers than 'KLEDH24733' |

'KLEDH24733' can be compared to the commercial *Dahlia* variety 'DAATTEN' (U.S. Plant Pat. No. 23,114). Differences between the varieties are described in Table 2.

TABLE 2

| Comparison with Similar Variety | | |
|---|---|---|
| Trait | Variety 'KLEDH24733" | Commercial line 'DAATTEN' |
| Vigor | Less vigorous than 'DAATTEN' | More vigorous than 'KLEDH24733' |

I claim:

1. A new and distinct variety of *Dahlia* plant named 'KLEDH24733' as shown and described herein.

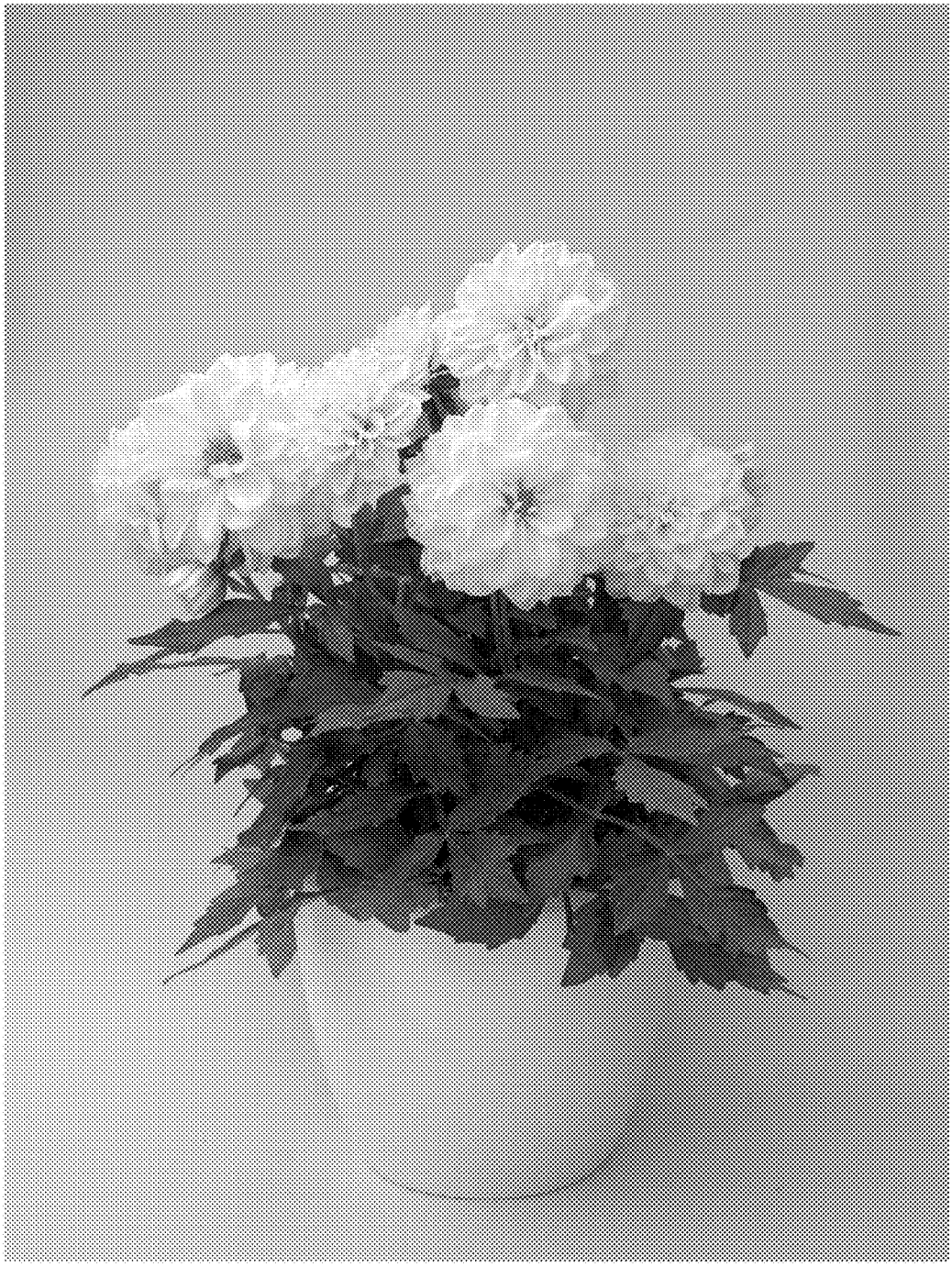

* * * * *